US012576435B2

(12) United States Patent　　　(10) Patent No.:　US 12,576,435 B2

Rodriguez　　　　　　　　　　　　(45) **Date of Patent:　*Mar. 17, 2026**

(54) MICROBIAL TREATMENT FOR WATER SYSTEMS AND SOIL REMEDIATION

(71) Applicant: NEW LIFE BIOSCIENCES LLC, The Woodlands, TX (US)

(72) Inventor: Marc Rodriguez, The Woodlands, TX (US)

(73) Assignee: New Life Biosciences LLC, The Woodlands, TX (US)

( * ) Notice: Subject to any disclaimer, the term of this patent is extended or adjusted under 35 U.S.C. 154(b) by 233 days.

This patent is subject to a terminal disclaimer.

(21) Appl. No.: 17/919,240

(22) PCT Filed: Apr. 15, 2021

(86) PCT No.: PCT/IB2021/053110

§ 371 (c)(1),
(2) Date: Oct. 14, 2022

(87) PCT Pub. No.: WO2021/209942

PCT Pub. Date: Oct. 21, 2021

(65) Prior Publication Data

US 2023/0331610 A1　　　Oct. 19, 2023

Related U.S. Application Data

(63) Continuation of application No. 17/195,214, filed on Mar. 8, 2021, which is a continuation-in-part of (Continued)

(51) Int. Cl.
*B09C 1/10*　　　　(2006.01)
*A61K 35/37*　　　(2015.01)
(Continued)

(52) U.S. Cl.
CPC ................ *B09C 1/10* (2013.01); *A61K 35/37* (2013.01); *B09C 1/002* (2013.01); *C02F 3/10* (2013.01);
(Continued)

(58) Field of Classification Search
CPC ........ A01N 63/28; A01N 63/22; A01N 25/00; A01N 37/44; C11D 3/221; C11D 3/33;
(Continued)

(56) References Cited

U.S. PATENT DOCUMENTS

| | | |
|---|---|---|
| 5,915,161 A | 6/1999 | Adams |
| 8,945,540 B2 | 2/2015 | Becquerelle |

(Continued)

FOREIGN PATENT DOCUMENTS

WO　　WO2014022692 A1　　2/2014

OTHER PUBLICATIONS

Chukwuma,A Review on Bacterial Contribution to Lignocellulose Breakdown into Useful Bio-Products, Environmental Research and Public Health (Year: 2021).*

(Continued)

*Primary Examiner* — Ekandra S. Miller-Cruz
(74) *Attorney, Agent, or Firm* — Cherskov Flaynik & Gurda, LLC

(57)　　　　　　　ABSTRACT

A method and composition are provided for breaking down a contaminant. A method for breaking down a contaminant in animal drinking water or an organic chemical agent includes providing a plurality of sporulated microbes. A composition for breaking down a contaminant in animal drinking water or an organic chemical agent includes a plurality of sporulated microbes.

21 Claims, 3 Drawing Sheets

Related U.S. Application Data application No. 16/849,823, filed on Apr. 15, 2020, now abandoned, said application No. PCT/IB2021/053110 is a continuation of application No. 16/849,823, filed on Apr. 15, 2020, now abandoned.

(60) Provisional application No. 62/986,499, filed on Mar. 6, 2020.

(51) Int. Cl.
| | |
|---|---|
| *B09C 1/00* | (2006.01) |
| *C02F 3/10* | (2023.01) |
| *C02F 3/34* | (2023.01) |
| *C02F 101/30* | (2006.01) |
| *C12N 1/20* | (2006.01) |

(52) U.S. Cl.
CPC .............. *C02F 3/341* (2013.01); *C02F 3/348* (2013.01); *C12N 1/20* (2013.01); *B09C 2101/00* (2013.01); *C02F 2101/306* (2013.01); *C02F 2305/06* (2013.01)

(58) Field of Classification Search
CPC ........... C11D 3/381; B09C 1/10; B09C 1/105; A61K 35/742; A61K 47/12; C05F 11/08; A61P 31/12; A61P 31/10; A61P 3/02; A61P 31/04; A61P 1/04; A61P 1/00; A23K 50/75; A23K 10/12; A23K 10/18; A23K 50/80; C09K 8/582; C02F 11/04; C02F 3/34; C02F 3/348; C02F 3/00; C02F 3/02; C12P 5/023; C12N 1/20; C12N 11/00; C12N 11/10
USPC ......................................................... 210/615
See application file for complete search history.

(56) References Cited

U.S. PATENT DOCUMENTS

| | | | |
|---|---|---|---|
| 9,771,602 B2 | 9/2017 | Anthony et al. | |
| 2003/0044382 A1* | 3/2003 | Selvig ................... | A01N 63/50 424/93.1 |
| 2008/0277338 A1 | 11/2008 | Whiteman | |
| 2011/0021401 A1 | 1/2011 | Scuilla | |

OTHER PUBLICATIONS

Tocheva, Polyphosphate Storage during Sporulation in the Gram-Negative Bacterium Acetonema Iongum, JorunalsASM.org (Year: 2013).*

Cartman, Bacillus subtilis Spores Germinate in the Chicken Gastrointestinal Tract, Applied and Environmental Microbiology, Aug. 2008, p. 5254â5258 (Year: 2008).*

Kari Rodriguez, International Search Report, International Application No. PCT/IB 21/53110, Date of Search: Jul. 14, 2021, Date Mailed: Jul. 28, 2021, ISA/US, Commissioner for Patents, Alexandria, Virginia.

\* cited by examiner

MICROBIAL TREATMENT FOR WATER SYSTEMS AND SOIL REMEDIATION

The present application claims priority to U.S. Utility application Ser. No. 16/849,823 filed on Apr. 15, 2020 and U.S. Utility application Ser. No. 17/195,214 filed on Mar. 6, 2021. The contents of the applications are hereby incorporated by reference.

FIELD

The present disclosure relates to methods and compositions for water and soil remediation. More specifically, the disclosure relates to methods and compositions for breakdown of contaminants using beneficial microbes.

BACKGROUND

Livestock such as cattle, horses, pigs, sheep, chickens, etc., require regular access to drinking water. Systems used to provide drinking water to livestock may be circulating water systems, a water supply to a tank, or a water tank, and can include a holding tank, trough or ball waterer for the livestock to access the drinking water.

The drinking water of livestock watering systems is subject to contamination. Contaminants may include algae, bacteria, protozoan parasites, helminth parasites, zoonotic pathogens and/or coliform bacteria. It is important to clean the drinking water to maintain livestock health. Typically cleaning animal drinking water is accomplished by periodic cleaning of watering systems, but this can be labor and time-intensive. For example, a livestock watering tank may need to be regularly drained and scrubbed to maintain a suitable and clean drinking water supply.

An object of the present disclosure is to provide a method and composition for cleaning animal drinking water that is effective and simple to carry out. A further object of the present disclosure is to provide a method and composition for breaking down ground contaminants.

SUMMARY

A further understanding of the functional and advantageous aspects of the invention can be realized by reference to the following detailed description and drawings.

An object of the present disclosure is to provide a method and composition for breakdown of contaminants using beneficial microbes.

Thus, by one broad aspect of the present invention, a method for treating drinking water for animals is provided, including providing a plurality of sporulated microbes to metabolize an organic matter in the drinking water.

By a further broad aspect of the present invention, a composition for treating animal drinking water is provided, including a plurality of sporulated microbes.

By a further broad aspect of the present invention, a method for breaking down an organic chemical agent is provided, comprising providing a plurality of sporulated microbes to the chemical agent.

By a further broad aspect of the present invention, a composition for breaking down an organic chemical agent is provided, comprising a plurality of sporulated microbes.

BRIEF DESCRIPTION OF THE DRAWINGS

Embodiments disclosed herein will be more fully understood from the following detailed description taken in connection with the accompanying drawings, which form a part of this application, and in which.

DETAILED DESCRIPTION

The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Various apparatuses or processes will be described below to provide examples of embodiments of the treatment method and system disclosed herein. No embodiment described below limits any claimed embodiment and any claimed embodiments may cover processes or apparatuses that differ from those described below. The claimed embodiments are not limited to apparatuses or processes having all of the features of any one apparatus or process described below or to features common to multiple or all of the apparatuses or processes described below.

Furthermore, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein.

Unless defined otherwise, all technical and scientific terms used herein are intended to have the same meaning as commonly understood to one of ordinary skill in the art.

"Organic chemical agent" as used herein means any carbon chain containing chemical, including but not limited to herbicides, insecticides, fungicides, and petroleum products.

"Microbes" as used herein include bacteria, fungi, algae, protozoa, and viruses.

A method and composition is provided in the present disclosure for cleaning animal drinking water or maintaining clean animal drinking water, by treatment with sporulated microbes. The sporulated microbes provide a stable format that is temperature and pressure resistant. Upon exposure to the drinking water, the sporulated bacteria are released and activated, and metabolize organic matter in the drinking water, thus cleaning the drinking water.

Figure 1:
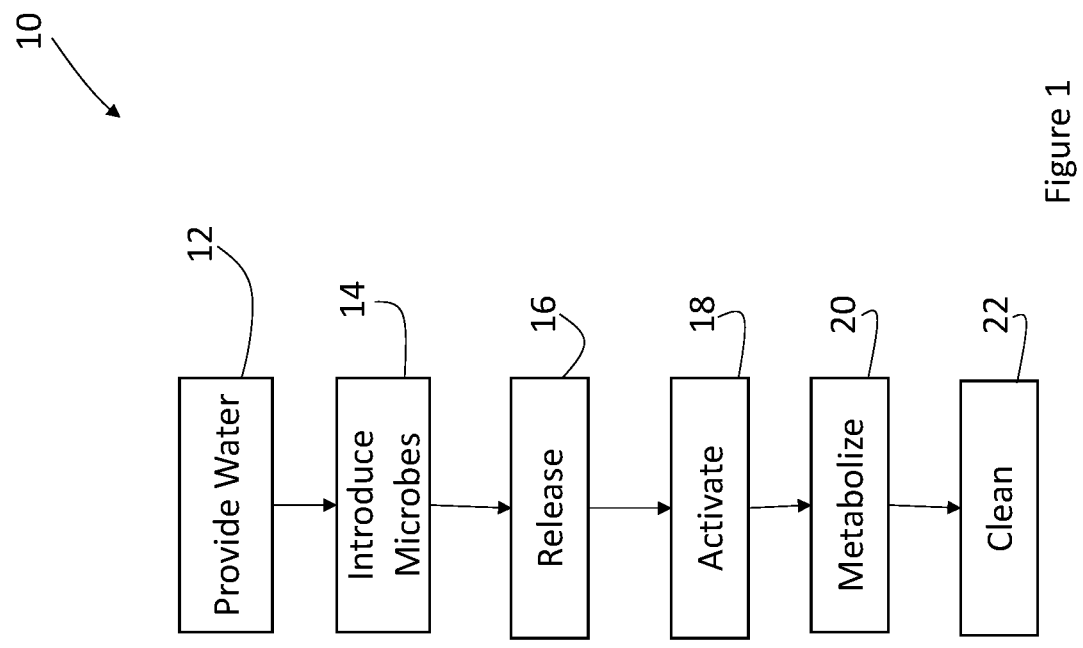
FIG. 1 is a flow chart of an embodiment of the system showing an overview of a method of treatment of livestock water, according to one embodiment of the invention.

As shown in the overview of FIG. 1, the method 10 comprises providing animal drinking water 12 in a container. Sporulated microbes are introduced 14 into the animal drinking water. In one embodiment, the microbes are released 16 and activated 18. The microbes metabolize 20 organic matter in the water thus cleaning 22 the drinking water.

Sporulated microbes form in response to inhospitable conditions, such as a severe lack of nutrients, that would be lethal for the normal (vegetative) form of the microbe. In the case of bacteria, the bacteria respond by producing and activating a protein that promotes the transcription of genes required for the conversion of the actively growing bacterium to a spore. During sporulation, the bacterial genome is duplicated and the second copy of the genome is enveloped together with some cytoplasm within an in-growth of the bacterial cell well. The resultant daughter cell is stabilized by formation of another membrane layer, a peptidoglycan material between the two membrane layers, and an outer coat of proteins, thereby forming an almost impregnable sphere. The mother cell dies and degrades, freeing the spore, which remains dormant until the environment becomes hospitable and the spore transforms back into a vegetative cell. Sporulated bacteria are stable throughout a range of conditions, which in the present disclosure provides an improved and advantageous format for the present application.

Bacteria are induced to be in the sporulated state by culture at high density (for example at $1.0 \times 10^{11}$ CFU/Gallon) in a media lacking nutrients, such as Tryptone, Soy and Proteins. The sporulated bacteria can be activated to come out of the dormant state in the presence of appropriate nutrients for the sporulated bacteria and/or in the presence of a higher pH.

To further enhance the beneficial effects of the sporulated microbes, other agents can be added with the microbes. These include an anti-pathogen agent to mitigate pathogens, such as protozoan parasites, helminth parasites, zoonotic pathogens and coliform bacteria. Additional agents include an animal digestive system enhancement agent (for example bacteria for digesting cellulose and lignan), an animal microbiome stability agent, an animal immune system support agent and a water contaminant mitigation agent. These additional agents are provided to the drinking water together with the sporulated microbes.

Water contamination mitigation agents may include nitrifying bacteria for oxidizing ammonia to nitrites and nitrites to nitrates. Water treatment using microbes can incorporate cleaning bacteria and nitrifying bacteria. Cleaning bacteria digest decomposing organic material, which produces ammonia, and assists nitrifying bacteria by preventing loss of oxygen caused by the decomposing material. Nitrifying bacteria include ammonia oxidizing bacteria that convert ammonia into nitrites, and nitrite oxidizing bacteria that convert nitrite into nitrate.

Water contamination mitigation agents may also include chelating agents for chelating metals and metalloids, such as arsenic and aluminum. Other water contamination mitigation agents are bacteria for metabolizing pesticides or herbicides, such as glyphosate, Dicamba, 2,4-dichlorophenoxyacetic acid, Atrazine, Fomesafen, Imidacloprid, Clothianidin or Thiamethoxam.

The sporulated microbes may be provided in a format such as a pellet, a tablet, a granule, a bolus, a spike, a mash, a crumble, a meal, a liquid, or a powder. In the case of a liquid, the sporulated microbes are at least $1 \times 10^{11}$ CFU/Gallon and a pH lower than 8.5, which maintains the sporulated bacteria in a dormant state.

In an embodiment of the present disclosure, the sporulated microbes are at least two of *Bacillus amyloliquefaciens, Bacillus subtilis, Rhodopseudomonas palustris*, and *Saccharomyces cerevisiae.*

To accomplish a preferred release rate or dosing rate, the sporulated microbes are adsorbed or packed with a carrier or provided in a format such as a tablet. The packing or carrier affects the rate of release of the microbes by providing a level of water accessibility or effervescence. With greater water accessibility or effervescence of the carrier, the microbes are released faster, and with lower water accessibility or effervescence, the release is slower and can be extended to at least 24 hours. The release rate can determine the CFU count in the treated drinking water, so different carriers can be utilized for different CFU concentration in the drinking water and different dosing characteristics. In addition, faster release tends to enable a greater concentration of the sporulated microbes and other additional agents towards the top of the water column of the drinking water, whereas slower release tends to enable a greater concentration of the sporulated microbes and additional agents towards the bottom of the water column of the drinking water. Slower release of the sporulated microbes also has an advantage of extending the water treatment time and requiring fewer additions of the treatment. Examples of carriers are salts and inert minerals such as zeolite and calcium byproducts.

In a further embodiment, a ratio of aerobic to anaerobic microbes is adjusted to target the condition of the water to be treated and attain a minimum CFU/Gallon of microbes in the drinking water. The ratio can be adjusted to take into account the water depth and level in the water column that is being targeted for treatment. Aerobic microbes will inhabit areas closer to the water surface, while anaerobic microbes will inhabit areas at greater water depth. Thus by providing a higher aerobic to anaerobic microbe ratio, a larger proportion of the microbes will be concentrated higher in the water column. Conversely, a lower aerobic to anaerobic microbes ratio will result in a larger proportion of the microbes lower in the water column. The anaerobic microbes are more effective in reducing organic matter. The aerobic microbes are more effective in treating adverse chemical conditions of the drinking water and are advantageous for animals to drink, for example to reduce coliforms. Thus the ratio of aerobic to anaerobic microbes can be customized to the water treatment required.

A composition for treating animal drinking water includes sporulated microbes as described above. The composition may further include an anti-pathogen agent, an animal digestive system enhancement agent, an animal microbiome stability agent, an animal immune system support agent, and/or a water contamination mitigation agent. Examples of a water contamination mitigation agent are a nitrifying bacteria, a chelating agent for a metal or a metalloid, and a bacteria for metabolizing a pesticide.

The composition for treating animal drinking water may be in the form of a pellet, tablet, granule, bolus, spike, mash, crumble, meal, liquid or powder. In liquid form, the liquid may preferentially be a solution with a concentration of the sporulated microbes of at least $1 \times 10^{11}$ CFU/gallon and a pH lower than 8.5.

Sporulated microbes that may be included in the composition are at least two of *Bacillus amyloliquefaciens, Bacillus subtilis, Rhodopseudomonas palustris*, and *Saccharomyces cerevisiae*. The composition may also include a carrier for the sporulated microbes. The characteristics of the carrier may be used to regulate the release rate of the microbes into the drinking water. The microbe composition may also be varied in the ratio of aerobic to anaerobic microbes, which would vary the distribution of the microbes once released into the drinking water.

Alternative Embodiment for Soil Remediation

An object of an alternative embodiment discussed herein is to provide a system and method for breakdown of agricultural products using beneficial microbes.

Organic chemical agents can be broken down by microbes, including a mixture of beneficial bacteria. The mixture of beneficial bacteria can include a first set of bacteria that break down the chemical agent and a further set of bacteria that, for example, break down the products of the first set of bacteria. This mixture of a plurality of bacteria may be referred to as a consortium of bacteria because the bacterial mixture works together more effectively than if it were added in parts. The effectiveness or efficacy of the bacterial consortium refers to the effectiveness of the bacterial consortium at breaking down the organic chemical agent. Likewise, the efficacy of the organic chemical agent refers to the effectiveness of the organic chemical agent at treating its target; for example, the efficacy of a herbicide at eliminating weeds. In order to stably formulate beneficial bacteria, the bacteria are sporulated to provide a stable format that is resistant to damage and is not active until distribution, for example, distribution on plants or soil.

Organic chemical agents may be an agricultural agent, a petroleum agent, an industrial site agent, or a metabolite or breakdown product of the chemical agent. Agricultural agents are, for example, herbicides, insecticides, or fungicides. Herbicides may include glyphosate, dicamba, 2,4-dichlorophenoxyacetic acid (also called 2,4-D), atrazine, fomesafen, triazine, or sulfonylurea herbicides; and insecticides may include neonicotinoids such as imidacloprid, clothianidin, and thiamethoxam. Organic chemical agents may occur for example, in agricultural settings, railroad right of ways, laneways, home and garden settings, golf courses, sign boulevards, road shoulders, powerline greenways, gas line right of ways, and water sources.

The treatment of a chemical agent may be done by adding the mixture of sporulated microbes to the organic chemical agent prior to distribution on plants or soil. The sporulated bacteria do not degrade the organic chemical agent prior to distribution because they remain in the dormant state. The sporulated bacteria remain dormant in the presence of the chemical agent until approximately 24 hours after the distribution of the mixture onto, for example, plants, such as agricultural crops or onto the soil. The lag time of approximately 24 hours for the sporulated bacteria to become active allows the chemical agent, which is typically active within one hour of application, to achieve its function, for example, as a herbicide or insecticide, before being degraded by the beneficial bacteria regenerated from the sporulated bacteria. The efficacy of the bacterial consortium at breaking down the chemical agent after activation is retained in the mixture because the bacteria is sporulated and thus stable. Likewise, the efficacy of the chemical agent is retained in the mixture because while in the mixture, the bacteria remains sporulated and inactive and thus does not break down the chemical agent.

Alternatively, the treatment of a chemical agent can be done by distributing the microbe mixture onto plants after the plants have been treated with the chemical agent. For example, an agricultural crop that is resistant to the chemical agent may be treated with the chemical agent, followed by a distribution of the microbe mixture to remove residual chemical agent or the metabolites of the chemical agent.

A further method is to treat the chemical agent by distributing the microbe mixture on soil that has been treated with the chemical agent, or on soil that is contaminated with the chemical agent.

In further examples, the sporulated microbes may be distributed on sidewalks, parks, residential lawns and driveways, sports fields, golf courses, or in water sources, such as water wells, wherein the site of distribution is a non-intended area for the chemical agent.

As a still further example, the sporulated microbes may be mixed with an agent, such as a drying agent, for spill cleanup to distribute on a chemical agent spill. Examples of drying agents are cat litter, corn cobs, and foam spray. The sporulated microbes may be impregnated into the drying agent in the packaging of the mixture before distribution of the mixture over the chemical agent spill.

The sporulated microbes may be in a pellet, powder, liquid, or granule format. The format allows a high concentration of the sporulated microbes that is sufficient to break down the chemical agent.

In one embodiment, the sporulated microbes are provided at a high enough concentration to break down the chemical agent on a plant crop, resulting in a reduction of the active form of the chemical agent in the plant food product.

In a further embodiment, the sporulated microbes are provided at a concentration that allows replanting of a crop in the treatment area after a set time, without risk of injury to the crop by the chemical agent or by the microbe mixture. The set time is shorter than if there was no treatment with the sporulated microbes. For example, the concentration of microbes may allow replanting a crop one month after treatment with the sporulated microbe mixture. The concentration of sporulated microbes may be determined by the amount of chemical agent that needs to be broken down, the type of chemical agent to be broken down, and the soil type that is being treated. As one example, the sporulated microbes may be in a solution with a concentration of at least $1 \times 10^{11}$ CFU/Gallon.

The sporulated microbes may be in a liquid format, at a pH lower than 8.5 or ideally at a pH between 4.5 and 5.5. In this format, the sporulated microbes do not degrade the organic chemical. Thus they can be mixed with the organic chemical agent prior to activation of the sporulated microbes without degradation of the organic chemical. This provides a useful format to package an organic chemical, such as a herbicide or insecticide, together with the dormant sporulated microbes, prior to application, for example, to agricultural crops.

After distribution onto, for example, plants or soil, the activated bacteria degrade the chemical agent by breaking down the carbon chain of the chemical agent or other covalent bonds that are metabolic targets of the active bacteria. Breakdown of the chemical bonds of the chemical agent may be carried out by enzymes secreted by the active bacteria. A mixture of at least two bacterial species is used to provide a broader spectrum of active proteins and enzymes to metabolize the organic chemical agent. The bacterial mixture also works synergistically such that one bacterial species may degrade metabolic products created by another bacterial species. In addition, enzymes secreted by one bacterial species may target degradation products of the organic chemical agent. Thus the combination of bacterial species provides greater activity than a simple additive advantage of individual species.

The sporulated microbes may be gram-negative and gram-positive bacteria that metabolize or break down a carbon bond or a covalent bond. The sporulated bacteria may be motile bacteria that metabolize or break down a carbon bond or a covalent bond. Further the sporulated bacteria may be *Bacillus* bacteria that metabolize or break down a carbon bond or a covalent bond.

The sporulated microbes may be a mixture of at least two of the following bacterial species: *Bacillus licheniformis;*

7

*Bacillus coagulans; Bacillus subtilis; Bacillus pumilus; Bacillus megaterium;* and *Bacillus amyloliquefaciens.*

In a further embodiment, cellulose- and lignan-composting bacteria may be included in the microbe mixture to break down crop waste such as dying material after a crop has been harvested and/or to break down weed waste.

The format provides an opportunity to premix other products into the formulation to provide an optimized formulation. An optimized sporulated microbe formulation includes the sporulated microbes and other ingredients that benefit the microbial activity, such as a nutrient, an extract, a sugar, or an activating agent of the sporulated microbes to provide a food source for the microbes and improve microbial performance.

An example embodiment of the present disclosure is provided below, including customer directions for a biological soil amendment for bio-remediation of pesticides and petroleum spills and residues.

In the example embodiment the product consists of a concentrated microbial powder which is a highly effective and concentrated biological amendment containing a broad spectrum of microbials specially selected for pesticide and petroleum remediation. The concentrated package of bacteria can be sprayed with water or mixed with all fertilizer types, bio-stimulants, or adjuvants to effectively and efficiently remove pesticide and petroleum residues and spills from soils.

Directions for use of the powder for broadcast or band boom applications: mix the concentrated powder in water soluble bag in spray tank that is half full. Add remaining mixture to fill tank. Mix thoroughly in tank before spraying. Spray volume per acre should be no less than 15 gallons per acre of finished spray. The product is compatible with all insecticides, herbicides, fungicides, adjuvants and fertilizers. Do not mix into a product that has a pH higher than 8.5. Alkaline products should be mixed with water to dilute the pH below 8.5 before adding the powder.

Directions for use of the powder for irrigation applications: mix the powder at well site in container to allow water soluble bags to dissolve and be mixed thoroughly before pumping through irrigation system. Can be applied with drip or foliar irrigation equipment. Do not apply with flood in-furrow irrigation. Can be applied in conjunction with all fertilizers or micronutrients formulations.

Application rates for the powder: half pound water soluble bag with concentrated powder will treat 5 acres at a final concentration of 750 billion CFU/Acre A two-pound packet with four half pound bags treats 20 acres with final concentration of 750 billion CFU/Acre For this embodiment, four to six applications per season are recommended for optimum results. Applying in conjunction with humic acids or other microbial food sources can be beneficial and recommended in low organic matter soils.

In one embodiment, the powder includes 75.50% inert ingredients and 24.5% of non-plant food ingredients, including the following soil health microbes:

*Bacillus licheniformis*——$5.8 \times 10^8$ CFU/Gm
*Bacillus coagulans*——$5.8 \times 10^8$ CFU/Gm
*Bacillus subtilis*——$5.8 \times 10^8$ CFU/Gm
*Bacillus pumilus*——$5.8 \times 10^8$ CFU/Gm
*Bacillus megaterium*——$5.8 \times 10^8$ CFU/Gm
*Bacillus amyloliquefaciens*——$5.8 \times 10^8$ CFU/Gm In one embodiment, the powder has a five-year shelf life if kept dry and does not require refrigeration. The end user is to follow SDS instructions for safety precautions, cleaning and PPE (Personal Protective Equipment). If no such instructions for washables, use detergent and hot water.

8

Figure 2A:
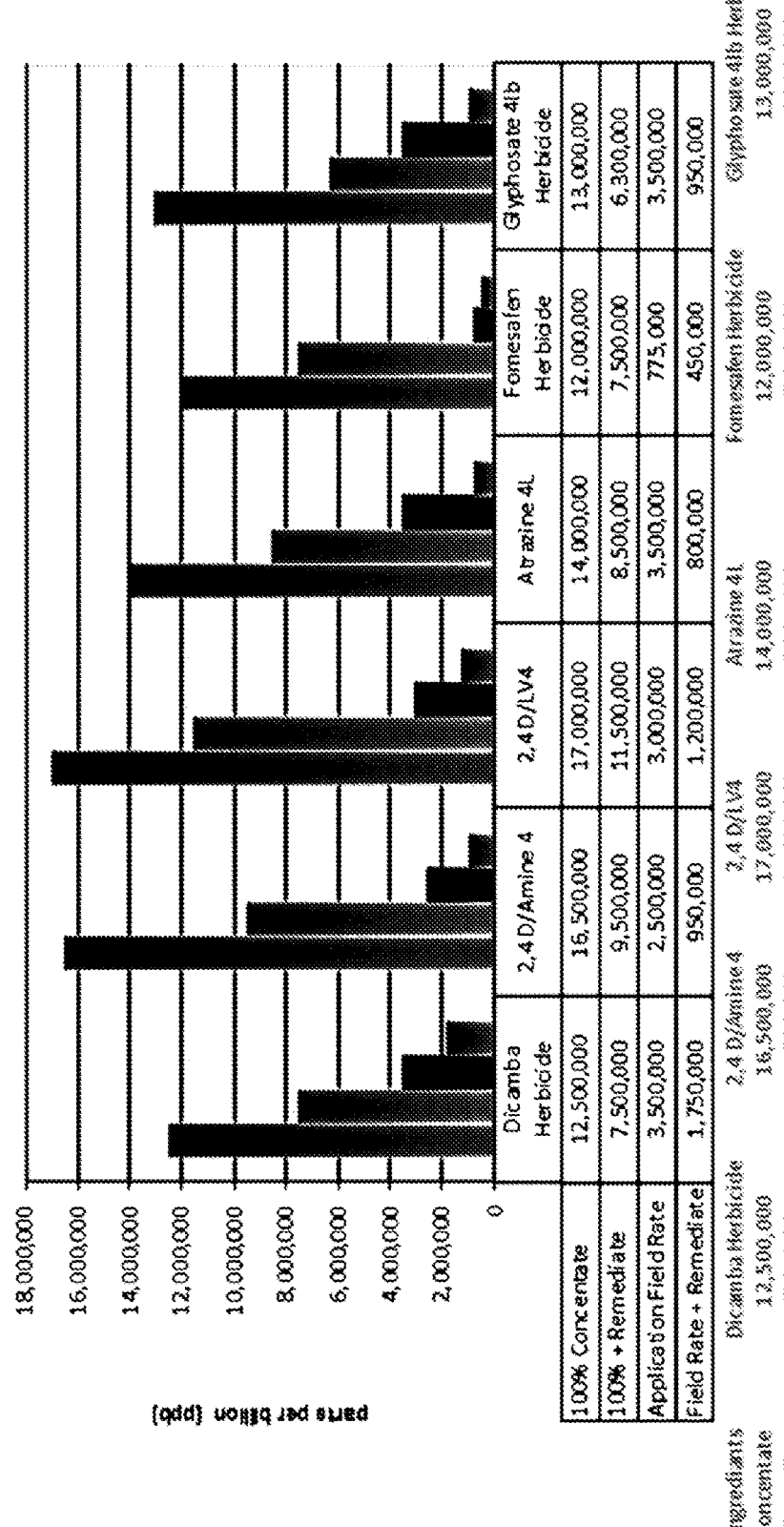
FIGS. 2A and 2B depict tables and graphical representation of results from a microbial treatment of organic chemical agents as an example of the method of the disclosure for an embodiment used for soil remediation.
Figure 2B:
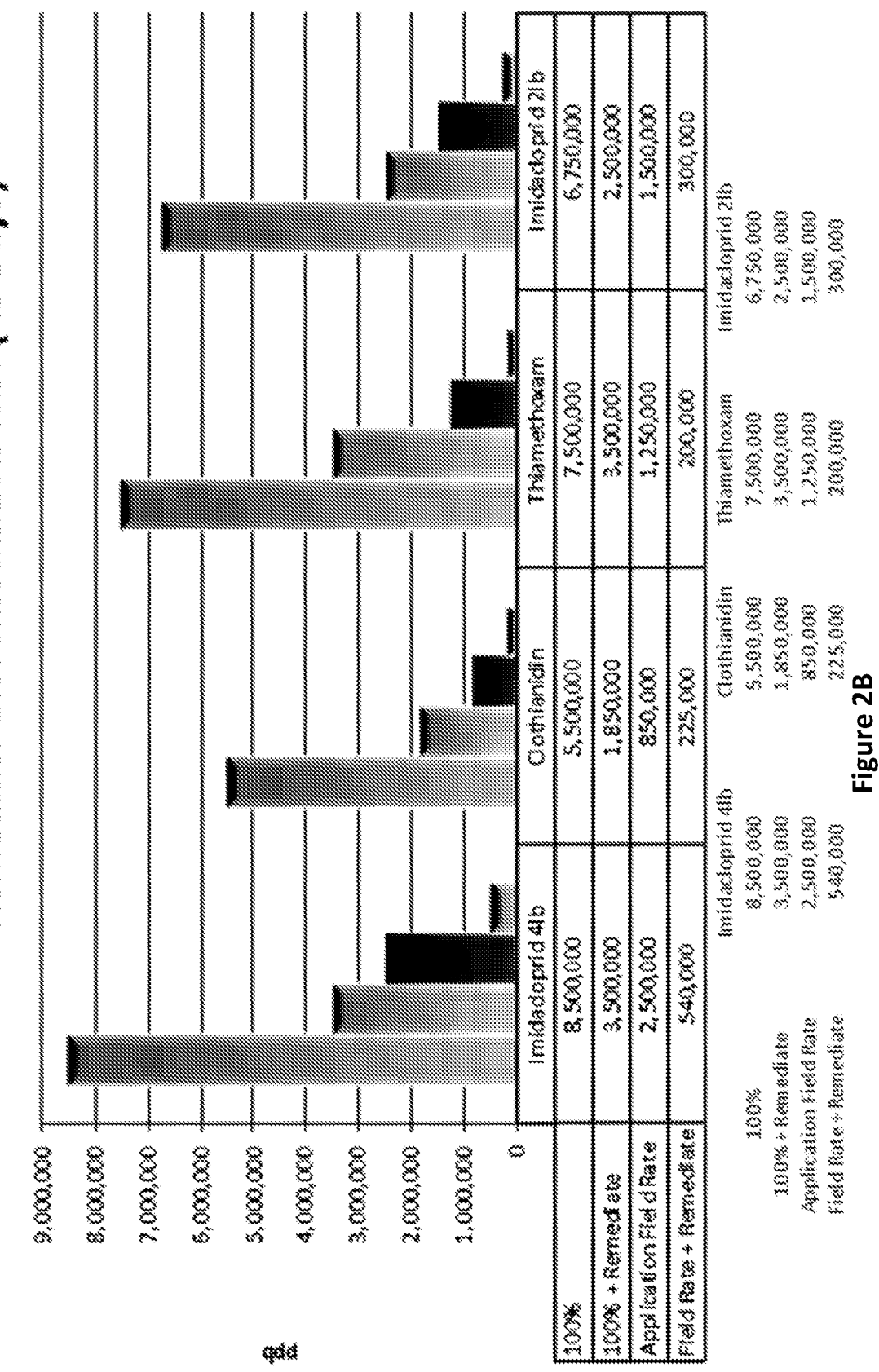

An example of the treatment of a variety of herbicides and insecticides is presented in FIGS. 2A and 2B. Chemical treatments, including the herbicides: glyphosate; Dicamba; 2,4-Dichlorophenoxyacetic acid (also called 2,4-D); Atrazine; and Fomesafen herbicide; and the insecticides: Imidacloprid; Clothianidin; and Thiamethoxam, were applied to the soil at an undiluted concentration (100%) or diluted as recommended by the manufacturer (Application Field Rate). After the soil was treated and dry (approximately 45 minutes after chemical treatment), the sporulated microbes were added. Samples were taken 45 days following treatment and analyzed for residual chemical. For each chemical and for both the undiluted chemical and the diluted chemical, the microbes are able to reduce the level of the organic chemical by at least 50% in 45 days.

A composition for the treatment of an organic chemical agent is made up of a consortium of sporulated microbes. In one embodiment, the composition may be a mixture of sporulated microbes and the organic chemical agent to be treated, both of which retain their efficacy when combined in the mixture. The mixture of sporulated microbes may be a solution with a density of at least $1 \times 10^{11}$ CFU/Gallon. The microbes are dormant in the composition, but able to be activated when the pH rises above 5.5 and/or when the bacterial spores are exposed to nutrients. The microbes in the composition may contain at least two of: *Bacillus licheniformis; Bacillus coagulans; Bacillus subtilis; Bacillus pumilus; Bacillus megaterium;* and *Bacillus amyloliquefaciens.*

In a further embodiment, the composition may include cellulose- and lignan-composting bacteria in the microbe mixture to break down dying material after a crop has been harvested and/or to break down weed waste.

The composition may also include a nutrient, an extract, or a sugar to improve microbial performance. An example would be to add seaweed extract.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

What is claimed is:

1. A method for breaking down an organic chemical agent, comprising mixing a plurality of sporulated microbes with the chemical agent, applying the mixture to a plurality of plants or a soil and activating the sporulated microbes to metabolize the chemical agent after applying the mixture, wherein the chemical agent comprises at least one of a herbicide, an insecticide, and a fungicide and wherein the sporulated microbes have a microbe efficacy and the chemical agent has a chemical agent efficacy, and wherein the sporulated microbes remain dormant before activation and for a delay period of at least 24 hours after application.

2. The method as in claim 1, wherein the chemical agent comprises at least one of:
an agricultural agent;
a petroleum agent;
an industrial site agent;

a metabolite of the chemical agent;

a herbicide;

an insecticide;

a fungicide;

glyphosate;

dicamba;

2,4-dichlorophenoxyacetic acid;

Atrazine;

fomesafen;

triazine;

sulfonylurea;

imidacloprid;

clothianidin; and thiamethoxam.

3. The method as in claim 1, wherein the mixture retains the microbe efficacy and the chemical agent efficacy.

4. The method as in claim 1, wherein the plurality of sporulated microbes comprises at least one of:

a pellet;

a powder;

a liquid; and granules.

5. The method as in claim 1, wherein providing the plurality of sporulated microbes comprises providing a concentration of sporulated microbes sufficient to break down the chemical agent.

6. The method as in claim 1, wherein providing the plurality of sporulated microbes comprises providing a concentration sufficient to reduce an active form of the chemical agent in a plant food product.

7. The method as in claim 5, wherein providing a concentration comprises providing a concentration that allows planting a crop after a set time without risk of an injury to the crop.

8. The method as in claim 7, wherein the plurality of sporulated microbes comprises a concentration of sporulated microbes based on at least one of:

an amount of the chemical agent;

a type of chemical agent; and a soil type.

9. The method as in claim 1, wherein the plurality of sporulated microbes comprises a solution with a concentration of sporulated microbes at least $1\times10^{11}$ CFU/Gallon.

10. The method as in claim 1, wherein the plurality of sporulated microbes comprises a solution with a pH lower than 8.5.

11. The method as in claim 1, wherein the sporulated microbes comprise gram-negative and gram-positive bacteria that metabolize a carbon bond or a covalent bond.

12. The method as in claim 1, wherein the sporulated microbes comprise motile bacteria that metabolize a carbon or a covalent bond.

13. The method as in claim 1, wherein the sporulated microbes comprise Bacillus bacteria that metabolize a carbon or a covalent bond.

14. The method as in claim 13, wherein the sporulated microbes comprise at least two of:

a. *Bacillus licheniformis;* b. *Bacillus coagulans;* c. *Bacillus subtilis;* d. *Bacillus pumilus;* e. *Bacillus megaterium*; and f. *Bacillus amyloliquefaciens.*

15. The method as in claim 11, wherein the sporulated microbes comprise cellulose and lignan composting bacteria, for breaking down at least one of crop waste and weed waste.

16. The method as in claim 1, wherein providing the plurality of sporulated microbes further comprises providing at least one of a nutrient, an extract, a seaweed, or a sugar as a food source for the microbes.

17. A composition for breaking down an organic chemical agent, the composition comprising a plurality of sporulated microbes and the chemical agent, wherein the chemical agent comprises at least one of a herbicide, an insecticide and a fungicide and wherein the sporulated microbes are dormant for at least 24 hours after application.

18. The composition as in claim 17, wherein the sporulated microbes comprise a solution with a density of at least $1\times10^{11}$ CFU/Gallon.

19. The composition of claim 17, wherein the plurality of sporulated microbes comprises at least two of:

a. *Bacillus licheniformis;* b. *Bacillus coagulans;* c. *Bacillus subtilis;* d. *Bacillus pumilus;* e. *Bacillus megaterium*; and f. *Bacillus amyloliquefaciens.*

20. The composition of claim 17, further comprising cellulose and lignan composting bacteria, for breaking down at least one of a crop waste and a weed waste.

21. The composition of claim 17, further comprising at least one of a nutrient, an extract, or a sugar as a food source for the microbes.

* * * * *